United States Patent [19]

Chen

[11] 4,082,747

[45] Apr. 4, 1978

[54] CHEMICAL PROCESS

[75] Inventor: Jong C. Chen, St. Louis, Mo.

[73] Assignee: Mallinckrodt, Inc., St. Louis, Mo.

[21] Appl. No.: 618,706

[22] Filed: Oct. 1, 1975

[51] Int. Cl.² ................................................ C07j 19/00
[52] U.S. Cl. ............................................,....... 260/239.57
[58] Field of Search ........................ 260/239.57, 112.5

[56] References Cited

U.S. PATENT DOCUMENTS

| | | | |
|---|---|---|---|
| 3,725,380 | 4/1973 | Konig et al. | 260/112.5 |
| 3,855,208 | 12/1974 | Rutner et al. | 260/239.57 |
| 4,013,688 | 3/1977 | Babcock et al. | 260/397.45 |

*Primary Examiner*—Elbert L. Roberts
*Attorney, Agent, or Firm*—Roy J. Klostermann

[57] ABSTRACT

An improved process for coupling an amino acid or derivative thereof to a cardiotonic glycoside derivative.

3 Claims, No Drawings

CHEMICAL PROCESS

BACKGROUND OF THE INVENTION

1. Field of the Invention

This invention is directed to a process for coupling an amino acid or derivative thereof to digitoxigenin, digoxigenin or a derivative of either.

2. Description of the Prior Art

Amino acids or derivatives thereof have been coupled to digitoxigenin or digoxigenin utilizing isobutylchloroformate, pivaloyl chloride or N-ethoxycarbonyl-2-ethoxy-1,2-dihydroquinoline. See for example U.S. Pat. No. 3,855,208 and Oliver et al. *J. Chem. Inv.* Vol. 47, pages 1035 – 1042 (1968).

However, when tyrosine methyl ester is coupled to 12 acetyl-3-succinyl-digoxigenin utilizing pivaloyl chloride to affect coupling, the reaction must be run at low temperatures and under anhydrous conditions in order to achieve acceptable yields. Furthermore, the desired reaction product must be usually isolated from a complex reaction mixture.

An improved process for coupling amino acids or derivatives thereof to digitoxin or digoxigenin would, therefore, be an advancement in the art.

BRIEF DESCRIPTION OF THE INVENTION

In accordance with this invention there is provided an improved process for coupling an amino acid or derivative thereof to digitoxigenin, digoxigenin or a derivative of either utilizing a carbodiimide to affect coupling.

By using the process of this invention the reaction may be run at room temperature, under atmospheric conditions with high yields.

DETAILED DESCRIPTION OF THE INVENTION

As mentioned the amino acids or derivatives thereof may be coupled directly to digoxigenin or digitoxigenin. Alternatively they may be coupled to half esters, dicarboxylic acids or substituted dicarboxylic acids of digitoxigenin, or digoxigenin. Useful half esters of digitoxigenin and digoxigenin include those wherein the dicarboxylic acid contains up to 10 carbon atoms such as phthalic, adipic, maleic, fumaric and glutaric. Of these acids, succinic, adipic and glutaric are preferred. Additionally digoxigenin, digitoxigenin, or the half esters thereof may be substituted in the 12 position with —OCOR$_1$, wherein R$^1$ is an alkyl group containing 1 to 4 carbon atoms with methyl being preferred.

Examples of amino acids or derivatives thereof that may be coupled to digitoxigenin or digoxigenin or a derivative of either include

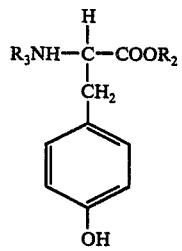

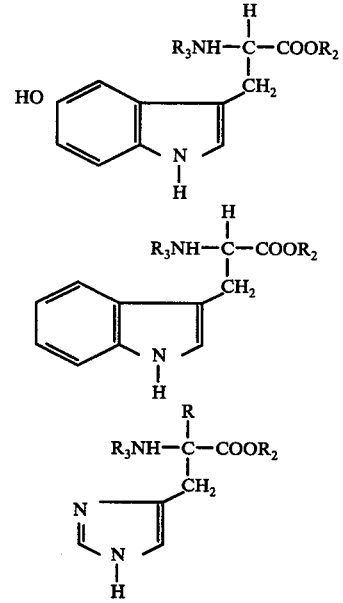

wherein R$_2$ is hydrogen or an alkyl group containing up to 6 carbon atoms and R$_3$ is a monoacyl radical of a dicarboxylic acid.

Examples of monoacyl radicals include those containing up to 10 carbon atoms such as fumaryl, succinyl, maleoyl, O-phthaloyl, adipyl or glutaryl.

Preferred amino acids include L-tyrosine, histidine, and 4-hydroxyphenyl glycine.

The carbodiimide useful to affect coupling in the present invention include those having the formula R$_4$—N=C=N—R$_5$ wherein R$_4$ and R$_5$ each independently is a cyclic or acyclic group. Cyclic groups include

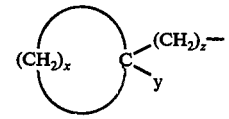

wherein x is an integer from 3 to 7, y is H or an alkyl group containing 1 to 10 carbon atoms preferably 1 to 5 carbon atoms and z is an integer from 0 to 5. Acylic groups include

wherein R$_6$ is a substituted or unsubstituted straight or branched chain carbon group containing 1 to 10 carbon atoms and y has the same significance as above. Generally R$_6$ is alkyl, dialkylaminoalkyl, di-alkylamino or morpholinoalkyl. Preferably, said alkyl group contains 1 to 5 carbon atoms.

Useful carbodiimides include dicyclohexylcarbodiimide 1-cyclohexyl-3-(2-morpholinoethyl)-carbodiimide
1-ethyl-3-(3-dimethylaminopropyl)-carbodiimide
1-butyl-3-(3-dimethylaminopropyl)-carbodiimide
1-pentyl-3-(5-diethylaminopentyl)-carbodiimide
1-nonyl-3-(2-dimethylaminoethyl)-carbodiimide Dicyclohexylcarbodiimide is preferred.

Generally, about 1 mole of the digitoxigenin, digoxigenin or a derivative thereof and about two moles of the amino acid or derivative thereof are used in the practice of this invention. Of course, more than 2 moles can be employed, but it provides no advantage. About 1 to 2 moles, preferably 1 to 1.1 mole of the dicarbodiimide per mole of digitoxigenin, digoxigenin or derivative thereof is used in the process of this invention. More than 2 moles can be used, but if does not provide any significant advantage.

A solvent must be used to dissolve the reactants. Any inert solvent which will solubilize (1) the digitoxigenin, digoxigenin or derivative thereof, (2) the amino acid or derivative thereof and (3) the coupling agent so the reaction will take place is suitable. Such solvents include dichloromethane, chloroform, ethyl acetate, dioxane, dimethylformamide or tetrahydrofuran.

The process of the present invention may be carried out at a temperature of from about 0° to about 100° C., preferably from about 10° to about 40° C. It may also be operated under anhydrous or atmospheric conditions.

In carrying out the process as is known to those skilled in the art, the reactants may be suitably brought together for example by mixing. The reaction product may be recovered by well known means such as preparative thin layer chromatography.

Surprisingly, when dicyclohexylcarbodiimide is used to affect couplings of tyrosine methyl ester to succinyl or adipyl digoxigenin, the yield is high and the desired product is a solid which can easily be recovered.

The invention will now be illustrated by the following examples:

EXAMPLE 1

3-succinyl-digoxigenin-L-tyrosine methyl ester

This compound was prepared according to the following sequence:

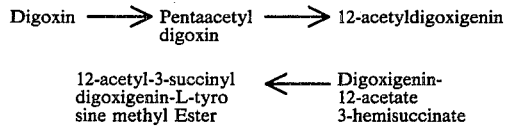

a. Pentaacetyl-digoxin

This compound was prepared by the procedure of H. W. Voigtlander and G. Balsam, Arch, Pharm., 301, 208 (1968).

A mixture of 1.8 g of digoxin, 40 ml of acetic anhydride and 30 ml of pyridine was heated at reflux under a nitrogen atmosphere for 90 minutes. The solvent was removed under reduced pressure and the residue was dissolved in chloroform. The chloroform solution was washed successively with aqueous sodium bicarbonate and 0.1N hydrochloric acid, dried over magnesium sulfate, and evaporated to leave the crude product, mp 95° – 116° C. No purification was done prior to the subsequent reaction.

b. 12-Acetyldigoxigenin

The crude acetylated product obtained above was heated at reflux for 45 min. in a mixture of 150 ml of methanol and 150 ml of 0.1N sulfuric acid. After evaporating the methanol at room temperature under reduced pressure, the product was extracted with chloroform. The chloroform layer was washed with saturated aqueous sodium bicarbonate, water, dried over magnesium sulfate and evaporated to leave a gummy residue which was recrystallized twice with acetone-petroleum ether to give 0.25 g of the desired product, mp 276° – 280°.

c. Digoxigenin-12-acetate-3-hemisuccinate

A solution of 880 mg of 12-acetyldigoxigenin and 880 mg of succinic anhydride in 10 ml of pyridine was heated at reflux under a nitrogen atmosphere for 7.5 hours. About 10 ml of saturated, aqueous sodium bicarbonate solution was added, and the solvents were evaporated. The residue was dissolved in water, washed thoroughly with ethyl acetate, acidified with hydrochloric acid at 0° C., and extracted with three portions of ethyl acetate. The combined extracts were washed with brine, dried over magnesium sulfate and evaporated to leave a residue which was purified by thin-layer chromatography (R$_f$ 0.18–0.36, acetone-hexane-petroleum ether, 10:7:3) to give 540 mg (49.8% yield) of the desired product, mp 110° – 120° C.

d. 12-Acetyl-3-succinyl-digoxigenin-L-tyrosine methyl ester

A mixture of 338.5 mg (0.636 mmole) of digoxigenin-12-acetate-3-hemisuccinate, 130.9 mg (0.636 mmole) of dicyclohexylcarbodiimide, 210 mg (1.076 mmole) of L-tyrosine methyl ester, 3 ml of dioxane and 5 ml of dichloromethane was stirred under nitrogen atmosphere at room temperature overnight. The urea formed was removed by filtration and the filtrate was diluted with dichloromethane, washed with diluted sodium bicarbonate solution, diluted hydrochloric acid, water, dried over magnesium sulfate and concentrated under reduced pressure. Purification of the residue by preparative tlc solvent system afforded 226 mg (50.1% yield) of the desired product, mp 109° – 113° C.

12-Acetyl-3-succinyl-digoxigenin-L-tyrosine methyl ester was also prepared according to a prior art procedure as follows.

A mixture of 22.4 mg of digoxigenin-12-acetate-3-hemi-succinate, 0.004 ml of triethylamine in 0.4 ml of dichloromethane and 0.00539 ml of pivaloyl chloride in 0.5 ml of dichloromethane was stirred at room temperature under nitrogen atmosphere for 15 min. and chilled to −10° C. prior to addition of a solution of 7.7 mg of L-tyrosine methyl ester in 0.2 ml pyridine. After stirring at −10° C. for 10 min. and at room temperature for 1 hr. the mixture was diluted with water, acidified with diluted hydrochloric acid at 0° C., and was extracted with dichloromethane. The extract was washed with aqueous sodium bicarbonate, water, dried over magnesium sulfate and concentrated under reduced pressure. A preparative silica gel tlc (acetone-petroleum ether-hexane, 8:3:7) of the residue gave five bands at R$_f$ 0.521–0.490, 0.472–0.412, 0.290–0.242, 0.170–0.109 and 0.0909–0.0667. The desired product (gum, 5.3 mg, 17.8% yield, R$_f$ 0.170–0.109) was collected and identified by ir, and UV spectroscopy.

EXAMPLE 2

3-adipyl-digoxigenin-L-tyrosine methyl ester

This compound was prepared according to the following sequence:

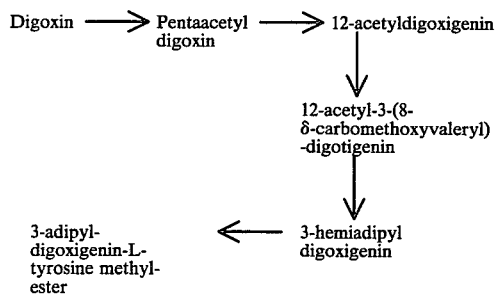

a. 12-Acetyl-3-(δ-carbomethoxyvaleryl)-digoxigenin

δ-Carbomethoxyvaleryl chloride (1g) was added to a stirred solution of 12-acetyldigoxigenin (2.16 g prepared in the same manner as given for succinyldigoxigenin-L-tyrosine) in pyridine (~15 ml) under nitrogen atmosphere. The reaction mixture was allowed to stand at room temperature for three hours and the crude product was taken up with ethyl acetate which was washed with 1N hydrochloric acid, saturated sodium bicarbonate and finally with water. The ethyl acetate solution was dried over anhydrous magnesium sulfate and the solvent was removed under reduced pressure. Purification of the residue by preparative tlc ($R_f$ = 0.206–0.135, acetone-hexane, 7:12) afforded 1.76 g of the desired product, m.p. 66 – 70° C.

b. 3-Hemiadipyl Digoxigenin

A mixture of 1.57 g of 12-acetyl-3-(δcarbomethoxyvaleryl)-digoxigenin, 6 g of potassium carbonate, and about 20 ml of methanol-water was stirred at room temperature for three hours. The methanol was removed at room temperature under reduced pressure and the aqueous solution was diluted with water, washed with ethyl acetate, acidified with cold hydrochloric acid and extracted with three portions of ethyl acetate. The combined extracts were washed with water, dried over magnesium sulfate and concentrated under reduced pressure. Purification of the residue by preparative tlc ($R_f$ 0.102 – 0.17, acetone-hexane, 1:1) gave 0.57 g of the desired acid, m.p. 75° – 95° C.

c. 3-Adipyl-digoxigenin-L-tyrosine methyl ester

A mixture of 323 mg of 3-hemiadipyl digoxigenin, 280 mg of L-tyrosine methyl ester, 210 mg of dicyclohexylcarbodiimide, 5 ml of dioxane and 10 ml of dichloromethane was stirred at room temperature overnight. The urea formed in the reaction mixture was removed by filtration and the filtrate was diluted with dichloromethane, washed with aqueous sodium bicarbonate, diluted hydrochloric acid, water, dried over magnesium sulfate and concentrated. Purification of the residue by preparative tlc ($R_f$ = 0.06 – 0.11, acetone-hexane, 10:9) gave 81.1 mg of desired compound, m.p. 89° – 104° C.

EXAMPLE 3

3-carbodigoxigenin-glycyl-L-tyrosine methyl ester

This compound was prepared according to the following sequence:

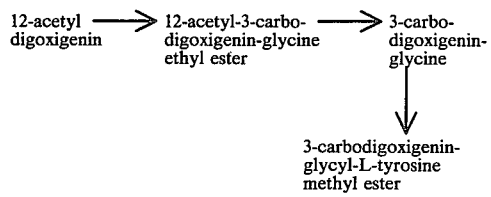

a. 12-Acetyl-3-carbodigoxigenin-glycine ethyl ester

A solution of 4 g of 12-acetyldigoxigenin prepared in the same manner as given for the succinyl derivative, 10 g of ethyl isocyanoacetate in 18 ml of dry pyridine was heated at reflux with stirring under anhydrous conditions for 5 hours. The pyridine was distilled off and the residue was taken up with ethyl acetate, washed with 1N hydrochloric acid, water, dried over magnesium sulfate and stripped of the solvent. The residue was purified by preparative tlc ($R_f$ = 0.30 – 0.38, acetone-hexane, (1:1) to give 5.96 g of the desired product, melting point 81° – 93° C.

b. 3-Carbodigoxigenin-glycine

A solution of 5.06 g of 3-carbodigoxigenin-glycine ethyl ester and 7.5 g of the potassium carbonate in 360 ml of methanol-water (1:1) was allowed to stand at room temperature. After 3 hours, the methanol was evaporated off and the aqueous solution was diluted with water, washed with ethyl acetate, acidified with cold, diluted hydrochloric acid and then extracted with three portions of ethyl acetate. The combined extracts were washed with water, dried over magnesium sulfate and concentrated to a small volume. The desired product (970 mg, melting point 233° – 236°) was precipitated and collected by filtration, washed with cold ethyl acetate, and dried in a vacuum desiccator.

c. 3-Carbodigoxigenin-glycyl-L-tyrosine methyl ester

A solution of 960 mg of 3-carbodigoxigenin-glycine, 960 mg of tyrosine methyl ester and 960 mg of dicyclohexylcarbodiimide in 960 ml of dichloromethane-dioxane (1:1) was stirred at room temperature overnight. The reaction mixture was filtered to remove the urea formed in the solution and the filtrate was diluted with ethyl acetate, washed with 1N hydrochloric acid, saturated sodium bicarbonate solution, water and dried over magnesium sulfate. Purification of residue by preparative tlc ($R_f$ = 0.185 – 0.318, acetone-hexane-acetic acid-methanol 25:25:1:2) gave 530 mg of the desired product, melting point 108° – 122°.

As various changes could be made in the above methods and products without departing from the scope of the invention, it is intended that all matter contained in the above description shall be interpreted as illustrative. It is to be understood therefore that the invention is not limited except as defined by the appended claims.

What is claimed is:

1. In a process for coupling tyrosine or tyrosine methyl ester to 3-carbodigoxigenin glycine, 3-hemiadipyl digoxigenin or digoxigenin-12-acetate-3-hemisuccinate in an inert solvent utilizing an agnet to affect coupling, the improvement comprising utilizing as the agent dicyclohexylcarbodiimide.

2. A process according to claim 1 wherein said dicyclohexylcarbodiimide is used in an amount from about 1 to 2 moles per mole of digoxigenin derivative.

3. A process according to claim 2 wherein the reaction temperature is from about 10° to about 40° C.